US010881058B2

(12) United States Patent
Li et al.

(10) Patent No.: US 10,881,058 B2
(45) Date of Patent: Jan. 5, 2021

(54) **BREEDING METHOD FOR TETRAPLOID *RICINUS COMMUNIS***

(71) Applicants: TIANJIN NANKAI UNIVERSITY CASTOR ENGINEERING SCIENCE AND TECHNOLOGY CO., LTD., Tianjin (CN); NANKAI UNIVERSITY, Tianjin (CN)

(72) Inventors: Xiulan Li, Tianjin (CN); Li Chen, Tianjin (CN); Feng Ye, Tianjin (CN); Lijian Dong, Tianjin (CN); Guangming Wang, Tianjin (CN)

(73) Assignee: TIANJIN NANKAI UNIVERSITY CASTOR ENGINEERING SCIENCE AND TECHNOLOGY CO., LTD, Tianjin (CN)

( * ) Notice: Subject to any disclaimer, the term of this patent is extended or adjusted under 35 U.S.C. 154(b) by 304 days.

(21) Appl. No.: 15/772,752

(22) PCT Filed: Aug. 11, 2016

(86) PCT No.: PCT/CN2016/094523

§ 371 (c)(1),
(2) Date: May 1, 2018

(87) PCT Pub. No.: WO2017/076094

PCT Pub. Date: May 11, 2017

(65) Prior Publication Data

US 2018/0317413 A1 Nov. 8, 2018

(30) Foreign Application Priority Data

Nov. 3, 2015 (CN) .......................... 2015 1 0735344

(51) Int. Cl.

| | |
|---|---|
| ***A01H 1/08*** | (2006.01) |
| ***A01H 6/38*** | (2018.01) |
| ***A01H 5/10*** | (2018.01) |
| *C12Q 1/6895* | (2018.01) |

(52) U.S. Cl.

CPC ................. *A01H 1/08* (2013.01); *A01H 5/10* (2013.01); *A01H 6/38* (2018.05); *C12Q 1/6895* (2013.01); *C12Q 2600/156* (2013.01)

(58) Field of Classification Search

CPC ........................................................ A01H 1/08

See application file for complete search history.

(56) References Cited

U.S. PATENT DOCUMENTS 8,946,513 B2 * 2/2015 Avidov .................... A01H 5/00
800/295

FOREIGN PATENT DOCUMENTS

| | | | |
|---|---|---|---|
| CN | 101124888 | A | 2/2008 |
| CN | 102159066 | A | 8/2011 |
| CN | 104082123 | A | 10/2014 |
| CN | 104488696 | A1 | 4/2015 |
| CN | 105230491 | A | 1/2016 |

OTHER PUBLICATIONS

International Search Report dated Nov. 18, 2016, issued in PCT Application No. PCT/CN2016/094523, filed Aug. 11, 2016.

* cited by examiner

*Primary Examiner* — Russell Kallis
(74) *Attorney, Agent, or Firm* — Workman Nydegger

(57) ABSTRACT

The present invention provides a breeding method for tetraploid ricinus communis. The method comprises: collecting a ricinus communis germplasm resource, performing morphologic character analysis and chromosome ploidy identification, selecting good diploid varieties, carrying out mutagenesis by using colchicine and oryzalin; performing chromosome ploidy identification on F1 generation seeds, selecting homozygous tetraploids, and performing economic character analysis and identification on the F2 generation, so as to breed good tetraploid ricinus communis.

8 Claims, 2 Drawing Sheets a b a b

BREEDING METHOD FOR TETRAPLOID *RICINUS COMMUNIS*

TECHNICAL FIELD

The present invention relates to a breeding method for new plantvarieties, in particular to a breeding method for new varieties (lines) of tetraploid *Ricinus communis* L.

BACKGROUND

*Ricinus communis* L., which is one of the top ten oil crops in the world, is widely used in national defense, aerospace, chemical medicine and machinery manufacturing. It is mainly characterized by not freezing at low temperatures (−18° C.) and not deteriorating and burning at high temperatures (500-600° C.), and it has important significance in national economic construction.

*Ricinus communis* L. resources are widely distributed in China and can be cultivated both in the northern and southern China. The annual planting area in China is 150,000 to 200,000 $hm^2$, and the annual output of *Ricinus communis* L. seeds is 150,000 to 250,000 tons. However, the annual demand for *Ricinus communis* L. seeds has exceeded 600,000 tons and the annual processing capacity of *Ricinus communis* L. seeds is above 1 million tons. The contradiction between supply and demand is becoming gradually prominent.

Although China has made remarkable achievements in the cross-breeding of *Ricinus communis* L. and the breeding of new varieties, the average yield is only about 400 kilograms per mu. According to the investigation and identification of the present applicants, both the cultivars and wild resources of *Ricinus communis* L. in China are diploid at present. Recent research data show that the higher plants living on Earth are all polyploids, and have undergone at least three whole genome doubling events from late Jurassic to Tertiary. Therefore, genome evolution is a common trend in the evolution of higher plants, and the resulting studies on genome polyploidization and polyploids have once again become hot spots in life science research. Polyploids are strong biological populations. The stress resistance is enhanced and the biological yield is significantly increased after polyploidization.

Chinese patent CN102159066 B reported a method for producing *Ricinus communis* L. seeds, characterized in that it comprises subjecting polyploid *Ricinus communis* L. plants to self-breeding or cross-breeding, wherein the polyploid *Ricinus communis* L. plants were obtained by the genomic multiplication of the *Ricinus communis* L. seeds of isogeneic diploid *Ricinus communis* L. ancestors, wherein the genomic multiplication is performed by the following steps: (a) applying a magnetic field to the diploid *Ricinus communis* L. seeds; and (b) contacting the *Ricinus communis* L. seeds with a microtubule polymerization inhibitor or microtubule assembly inhibitor in the magnetic field to obtain polyploid *Ricinus communis* L. seeds. The polyploid *Ricinus communis* L. plants produced by the polyploid *Ricinus communis* L. seeds have at least the same breeding ability as the isogeneic diploid *Ricinus communis* L. ancestors. The polyploid *Ricinus communis* L. plants are tetraploid.

However, it is still blank in the breeding of *Ricinus communis* L. polyploids in China and no relevant reports have been found yet because the mutagenesis of *Ricinus communis* L. polyploids is very difficult. The difficulties in the breeding of *Ricinus communis* L. polyploids lie in that the *Ricinus communis* L. seeds are very special in structure, can store rich nutrients that are sufficient to meet the requirement for nutrition until 4 true leaf stage, and therefore are difficult to absorb external mutagens, resulting in that the mutagenesis of *Ricinus communis* L. tetraploids is very difficult.

SUMMARY OF THE INVENTION

The object of the present invention is to provide a breeding method for tetraploid *Ricinus communis* L. In the method, mixed mutagens are employed, and the endosperms are removed during the germination of the *Ricinus communis* L. seeds to force the naked embryos to absorb mutagens to interrupt the formation of spindles, which greatly increase the frequency of mutagenesis and result in a new line of homozygous *Ricinus communis* L. tetraploids in China for the first time. Chromosome analysis and identification performed on F1 young leaves demonstrate the reduced confounding of chimeras and aneuploids and the great improvement in the screening frequency of homozygous tetraploids. New lines (varieties) of tetraploid *Ricinus communis* L. with excellent traits can be developed in 3-4 years through the analysis and selection of F2 plants in terms of economical traits.

The breeding method for tetraploid *Ricinus communis* L. provided by the present invention comprises the following steps: selecting excellent diploid *Ricinus communis* L. varieties as materials for tetraploid mutagenesis by subjecting *Ricinus communis* L. to morphological analysis and chromosomal ploidy identification on the basis of the collection of *Ricinus communis* L. germplasm resources throughout China and the establishment of *Ricinus communis* L. germplasm resources nursery; subjecting the naked *Ricinus communis* L. embryos resulting from artificial removal of the *Ricinus communis* L. endosperms to a forced absorption method with mixed mutagens to perform a doubling process for tetraploidization, subjecting the newborn F1 young leaves to chromosome analysis and ploidy identification, removing chimeras and aneuploids, screening for homozygous *Ricinus communis* L. tetraploid plants, which are then subjected to large-scale planting and cultivation management according to conventional methods for cultivating *Ricinus communis* L.

The breeding method for tetraploid *Ricinus communis* L. provided by the present invention comprises the following steps:

1) firstly, extensively collecting the cultivars and wild resources of *Ricinus communis* L. in China and establishing *Ricinus communis* L. germplasm resources nursery;
2) subjecting the *Ricinus communis* L. germplasm resources to cytological analysis and chromosomal ploidy identification; preparing chromosome specimens of *Ricinus communis* L. through a wall degradation hypotonic method utilized in the preparation of chromosome specimens of plants. The basic number of the *Ricinus communis* L. chromosome is x=10, and the diploid chromosome number of somatic cells is 2n=2x=20;
3) selecting excellent diploid *Ricinus communis* L. lines according to the results of morphological analysis, economic characteristic analysis and ploidy identification; selecting diploid *Ricinus communis* L. varieties with excellent agronomic characteristics as materials for inducing tetraploid *Ricinus communis* L.;

4) subjecting the seeds to sterile disinfection by using conventional disinfection methods, then removing the endosperms, stripping the seed embryos out, placing them into 1/2MS medium, and incubating under conditions of 23° C.±2° C. without lighting until the seed embryos have germinated;

the conventional disinfection method is as follows: disinfecting with 75% alcohol for 60 seconds, rinsing with sterile water, and then disinfecting with 2% sodium hypochlorite for 15 minutes, rinsing with sterile water for 3 times;

5) performing artificial mutagenesis of tetraploids: transferring into a solution containing mixed mutagens of colchicine and oryzalin at a certain mass concentration, to perform a doubling process in darkness at a lower temperature of 15-20° C. for 48-72 hours; the final concentration of the mixed mutagens is 0.01%; the mass concentrations of the colchicine and the oryzalin in the solution are 0.02%, respectively;

6) transferring into 1/2MS medium, to continue to cultivate at 23° C.±2° C. with a lighting of 1000 Lux, 16 hours/day;

7) transplanting the seedlings in bottles into disinfected soil when the seedlings have developed into 4 true leaf stage and the roots have a length of 3-5 cm; at 3 days before transplanting, opening the caps of bottles for acclimatization; during management stage of the transplanted seedlings: the doubling treated seedlings have been largely damaged and grow slowly, and thus a carefully management is required, and the control of temperature and humidity should be strengthened in order to reduce the abnormal death of seedlings to make the survival rate achieve above 90%;

the conditions for the management of the transplanted seedlings are as follows: maintaining the temperature at 25° C.±2° C., the humidity at 65%±5, the soil condition is normal sandy loam;

8) subjecting the newborn young leaves of F1 embryos to chromosome analysis and ploidy identification, removing chimeras and aneuploids, screening for homozygous tetraploid plants; the steps of chromosome analysis and ploidy identification are as follows: harvesting newborn young leaves at 8-9 a.m., pre-processing with 0.002M 8-hydroxyquinoline for 3-4 hours, then preparing chromosome specimens of *Ricinus communis* L. through a wall degradation hypotonic method utilized in the preparation of chromosome specimens of plants, removing chimeric and aneuploid plants, screening for plants whose somatic cell chromosome is 2n=4x=40 to obtain homozygous tetraploid plants.

9) large-scale planting and cultivation management of the tetraploid *Ricinus communis* L. according to conventional methods for cultivating *Ricinus communis* L., subjecting the F1 seeds of tetraploid *Ricinus communis* L. to chromosome analysis and ploidy identification again, removing chimeras and aneuploids, performing repeated identification as chimeras and aneuploids may exist in F1 generation at lower frequency, screening for new homozygous tetraploid *Ricinus communis* L. germplasms.

The term "Oryzalin" is also known as "SHUIDAOSU"; the Chinese alias is ANHUANGLELING and ANHUANGLING; the Trade name is Surflan, and the manufacturer is Dow Agrosciences company, US, and it has a chemical nameof 3,5-dintro-N4,N4-dipropyl sulfanilamide, and a chemical structure of:

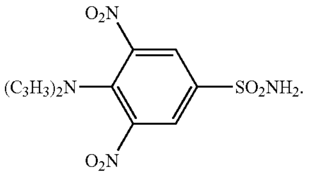

The present invention provides a breeding method for tetraploid *Ricinus communis* L. The mutagenesis frequency of tetraploid *Ricinus communis* L. is increased and the mutagenesis rate achieves about 50% by removing the endosperms and forcing the seed embryos to directly absorb mutagens. At the same time, the *Ricinus communis* L. has a robust root system which has strong ability to absorb mutagens, so that the roots can be easily doubled, resulting in high mutagenesis frequency of polyploids and chimeras in roots. Therefore, roots cannot be used as materials for ploidy identification. In the present invention, F1 young leaves are used as materials for chromosome ploidy identification, which can effectively exclude the chimeras and aneuploids, and greatly improve the screening frequency of homozygous tetraploids.

DETAILED DESCRIPTION

The prominent features and significant advances of the present invention can be presented in the following examples without any limitation of the invention.

Figure 4:
FIG. 4 shows the picture of *Ricinus communis* L. germplasm resources nursery.

A breeding method for tetraploid *Ricinus communis* L. provided by the present invention comprises the following steps:

1) collecting germplasm resources:

collecting 49 cultivars and wild resources of *Ricinus communis* L. from different regions of China and 5 foreign varieties (see table 1), including Yunnan, Sichuan, Jiangsu, Xinjiang, Shandong, Shanxi, Hebei, Tianjin of China and Israel and France, etc., to establish Ricinus communis L. germplasm resources nursery (see FIG. 4);

TABLE 1

Types, varieties and sources of 54 *Ricinus communis* L. germplasm resources

| NO. | type | variety | source |
|---|---|---|---|
| 01 | wild | Yun-R 2014115 | Yunnan |
| 02 | cultivated | Ya-R No. 1 | Sichuan |
| 03 | cultivated | large grain type of *Ricinus communis* L. | Jiangsu |
| 04 | variety | Yun-R No. 4 | Shanxi |
| 05 | variety | Yun-R No. 5 | Shanxi |

TABLE 1-continued

| Types, varieties and sources of 54 *Ricinus communis* L. germplasm resources | | | |
|---|---|---|---|
| NO. | type | variety | source |
| 06 | variety | Fen-R No. 10 | Shanxi |
| 07 | variety | economic *Ricinus communis* L. No. 1 | Shanxi |
| 08 | variety | economic *Ricinus communis* L. No. 2 | Shanxi |
| 09 | variety | Zhongbei No. 3 | Shanxi |
| 10 | variety | Zhongbei No. 4 | Shanxi |
| 11 | variety | Tong-R No. 9 | Neimeng |
| 12 | variety | Tong-R No. 10 | Neimeng |
| 13 | variety | $KB_2$ | Xinjiang |
| 14 | variety | Green-R No. 1 | Tianjin |
| 15 | variety | Green-R No. 2 | Tianjin |
| 16 | variety | Zi-R No. 1 | Shandong |
| 17 | variety | Zi-R No. 2 | Shandong |
| 18 | variety | Zi-R No. 3 | Shandong |
| 19 | variety | Zi-R No. 4 | Shandong |
| 20 | variety | Zi-R No. 5 | Shandong |
| 21 | variety | Zi-R No. 7 | Shandong |
| 22 | variety | Zi-R No. 8 | Shandong |
| 23 | variety | Zi-R No. 9 | Shandong |
| 24 | hybrid | 89-3 × S207 | Shandong |
| 25 | hybrid | Jiaxiang No. 2 | Shandong |
| 26 | hybrid | C205 × 1002E | Shandong |
| 27 | hybrid | CS219 × E088 | Shandong |
| 28 | hybrid | CS219 × 9018 | Shandong |
| 29 | hybrid | C208 × 9018 | Shandong |
| 30 | hybrid | C208 × E06 | Shandong |
| 31 | hybrid | Tian 1-8 × E06 | Shandong |
| 32 | hybrid | Tian 2-18 × S206 | Hainan |
| 33 | hybrid | Tianqi × 101 Feng | Hainan |
| 34 | hybrid | Tian 2-18 × E07 | Shandong |
| 35 | hybrid | 1002 × E06 | Shandong |
| 36 | hybrid | 1002 × 9018 | Shandong |
| 37 | hybrid | 904 × E088 | Shandong |
| 38 | hybrid | 9041C × E07 | Shandong |
| 39 | hybrid | 1002 × 101 | Shandong |
| 40 | hybrid | C205 × 干10 | Shandong |
| 41 | hybrid | C213 × E088 | Shandong |
| 42 | hybrid | Tian 1-8 × Qiongxi × E088 | Shandong |
| 43 | hybrid | Tian 2-18 × S206 | Shandong |
| 44 | hybrid | 9041C × Cai 07 | Shandong |
| 45 | hybrid | C208 × 101 | Shandong |
| 46 | variety | Hang-R N0. 8 | Shandong |
| 47 | variety | Hang-R N0. 10 | Shandong |
| 48 | variety | Hang-R N0. 11 | Shandong |
| 49 | farm variety | Qianxi-2015504 | Hebei |
| 50 | foreign variety | C855 | Israel |
| 51 | foreign variety | KA93 | Israel |
| 52 | foreign variety | dwarf-2014309 | France |
| 53 | foreign variety | dwarf-2014411 | France |
| 54 | foreign variety | dwarf-2014412 | France |

2) subjecting the *Ricinus communis* L. germplasm resources to cytological analysis and chromosomal ploidy identification: preparing chromosome specimens of *Ricinus communis* L. through a wall degradation hypotonic method utilized in the preparation of chromosome specimens of plants. The basic number of the *Ricinus communis* L. chromosome is x=10, and the diploid chromosome number of somatic cells is 2n=2x=20;

3) selecting excellent diploid *Ricinus communis* L. lines according to the results of morphological analysis, economic characteristic analysis and chromosomal ploidy identification; selecting excellent diploid *Ricinus communis* L. varieties as materials for inducing tetraploids;

4) subjecting the seeds to sterile disinfection by using conventional disinfection methods, then removing the endosperms, stripping the seed embryos out, placing them into 1/2MS medium, and incubating under conditions of 23° C.±2° C. without lighting until the seed embryos have germinated;

the conventional disinfection method is as follows: disinfecting with 75% alcohol for 60 seconds, rinsing with sterile water, and then disinfecting with 2% sodium hypochlorite for 15 minutes, rinsing with sterile water for 3 times;

5) performing artificial mutagenesis of tetraploids: transferring the germinated young embryos into a solution containing mixed mutagens of colchicine and oryzalin at a certain mass concentration, to perform a doubling process in darkness at a lower temperature of 15-20° C. for 48-72 hours;

the mixed mutagens were prepared as follows: firstly, preparing 0.02% colchicine (mass percentage concentration) and 0.02% oryzalin solutions, respectively, and then mixing them at a volume ratio of 1:1, resulting in that the final concentrations of the colchicine and oryzalin were 0.01% respectively;

6) transferring into 1/2MS medium, to continue to cultivate at 23° C.±2° C. with a lighting of 1000 Lux, 16 hours/day;

7) transplanting the seedlings into disinfected soil when their true leaves have achieved more than 4 and their root systems have developed to normal; at 3 days before transplanting, opening the caps of bottles for acclimatization. The doubling treated seedlings have been largely damaged. Thus, the management should be strengthened after transplanting, by maintaining the temperature at 25° C.±2° C., and the humidity at about 65%, to reduce the abnormal death of the seedlings.

8) chromosome analysis and ploidy identification: harvesting newborn young leaves at 8-9 a.m., pre-processing with 0.002M 8-hydroxyquinoline for 3-4 hours, then preparing chromosome specimens of *Ricinus communis* L. through a wall degradation hypotonic method utilized in the preparation of chromosome specimens of plants, removing chimeric and aneuploid plants, screening for plants whose somatic cell chromosome is 2n=4x=40 to obtain homozygous tetraploid plants, continue to cultivate the seedlings;

9) large-scale transplantation: performing large-scale planting and cultivation management according to conventional methods for cultivating *Ricinus communis* L., subjecting the F1 seeds of tetraploid *Ricinus communis* L. to chromosome analysis and ploidy identification again, removing chimeras and aneuploids, performing repeated identification as chimeras and aneuploids may exist in the F1 generation of *Ricinus communis* L. at lower frequency, screening for new homozygous tetraploid *Ricinus communis* L. germplasms.

SPECIFIC APPLICATION EXAMPLE 54 cultivars and wild resources of *Ricinus communis* L. were collected from different regions of China from May to December 2013. Firstly, they were subjected to chromosome analysis and ploidy identification to ensure the basic number of the *Ricinus communis* L. chromosome is x=10 and the chromosomes of somatic cells are all diploid, i.e. 2n=2x=20. In April 2014, excellent diploid *Ricinus communis* L. selected from the above germplasm resources were used as raw materials for artificial mutagenesis of tetraploids. Firstly, the seeds were subjected to sterile disinfection by using conventional disinfection methods, i.e. disinfecting with 75% alcohol for 60 seconds under sterile condition, rinsing with sterile water, disinfecting with 2% sodium hypochlorite for 15 minutes, rinsing with sterile water for 3 times. Then the endosperms were removed, and the seed embryos were stripped out and were placed into 1/2MS medium to incubate under conditions of 23° C.±2° C. without lighting until the seed embryos had germinated. Then artificial mutagenesis of tetraploids was performed: the germinated young seed embryos were transferred into a solution containing mixed mutagens of colchicine and oryzalin at a certain mass concentration, to perform a doubling process in darkness at a lower temperature of 15-20° C. for 48-72 hours, and subsequently transferred into 1/2MS medium, to continue to cultivate at 23° C.±2° C. with a lighting of 1000 Lux, 16 hours/day.

The mixed mutagens were prepared as follows: firstly, preparing aqueous solutions of 0.02% colchicine (mass percentage concentration) and 0.02% oryzalin, respectively, and then mixing them at a volume ratio of 1:1, resulting in that the final concentrations of the colchicine and oryzalin were 0.01% respectively.

Figure 1:
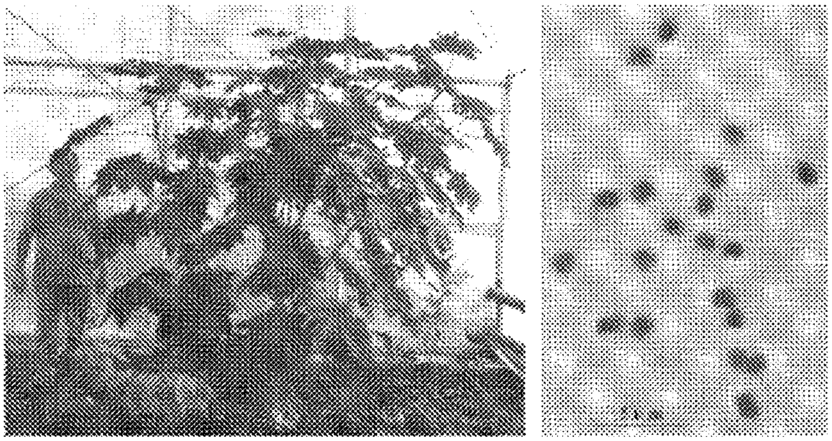
FIG. 1 shows the appearance of diploid *Ricinus communis* L. plants (a) with a chromosome number of 2n=2x=20 (b).
Figure 2:
FIG. 2 shows the appearance of tetraploid *Ricinus communis* L. plants (a) with a chromosome number of 2n=4x=40 (b).
Figure 3:
FIG. 3 shows the comparison of appearance between diploid *Ricinus communis* L. seeds (b) and tetraploid *Ricinus communis* L. seeds (a).

In May 2014, the seedlings, as the materials for artificial mutagenesis, were transplanted, and then were individually identified for the ploidy, i.e., pre-process: young leaves were harvested at 8-9 a.m. and placed into 0.002M 8-hydroxyquinoline at 20-22° C. for 3-4 hours→pre-hypotonic treatment: hypotonic treatment with 0.075M KCl at 22° C. for 15 minutes→wall degradation: enzymatic treatment with 2.5% mixed enzymes (pectinase+cellulase) at 25° C. for 60 minutes→post-hypotonic treatment: hypotonic treatment with 0.075M KCl at 25° C. for 15 minutes→fixing: performing fixing treatment with a fixing solution of 3:1 (methanol:glacial acetic acid) for above 30 minutes→preparation of chromosome specimen→staining: staining with a staining solution of 40:1 (phosphate buffer : Giemsa) for 60 minutes→observation with microscope, chromosome analysis and ploidy identification were performed, homozygous tetraploid plants were selected and chimeric and aneuploid plants were eliminated. In June 2014, the homozygous tetraploid plants were subjected to large-scale planting and cultivation management according to conventional methods for cultivating *Ricinus communis* L. In October 2014, F1 seeds of the tetraploid *Ricinus communis* L. were harvested. In December 2014, the seeds of tetraploid *Ricinus communis* L. were subjected to chromosome analysis again to eliminate the chimeras and aneuploids that may exist in the F1 seeds at low frequency. In April 2015, the tetraploid *Ricinus communis* L. were planted on large-scale (see FIGS. 1 to 3 for a comparison result of diploid *Ricinus communis* L. and tetraploid *Ricinus communis* L.).

In the method, mixed mutagens are employed and the endosperms are removed during the germination of the *Ricinus communis* L. seeds to force the naked embryos to absorb mutagens to interrupt the formation of spindles, which greatly increase the frequency of mutagenesis and result in a new line of homozygous *Ricinus communis* L. tetraploids in China for the first time. Chromosome analysis and identification performed on F1 young leaves demonstrate the reduced confounding of chimeras and aneuploids and the great improvement in the screening frequency of homozygous tetraploids.

The invention claimed is:

1. A breeding method for tetraploid *Ricinus communis* L., comprising the following steps:

providing diploid *Ricinus communis* L. seeds, subjecting the naked embryos of the *Ricinus communis* L. seeds obtained after artificial removal of endosperms to a forced absorption method with mixed mutagens to perform a doubling process for tetraploidization, subjecting the newborn F1 young leaves to chromosome analysis and ploidy identification, removing chimeras and aneuploids, and screening for homozygous tetraploid plants, which are then subjected to large-scale planting and cultivation management according to conventional methods for cultivating *Ricinus communis* L.

2. The breeding method for tetraploid *Ricinus communis* L. according to claim 1, wherein the mixed mutagens are a mixed solution of colchicine and oryzalin.

3. The breeding method for tetraploid *Ricinus communis* L. according to claim 1, wherein the basic number of the *Ricinus communis* L. chromosome is x=10, and the diploid chromosome number of somatic cells is 2n=2x=20.

4. A breeding method for tetraploid *Ricinus communis* L., comprising the following steps:

1) providing diploid *Ricinus communis* L. seeds;

2) subjecting the *Ricinus communis* L. seeds to sterile disinfection using conventional disinfection methods, then removing the endosperms, stripping the seed embryos out, placing the seed embryos into 1/2MS medium, and incubating the seed embryos at 23° C.±2° C. without lighting until the seed embryos have germinated;

3) transferring into an aqueous solution containing mixed mutagens of colchicine and oryzalin at a certain mass concentration, to perform a doubling process in darkness at a lower temperature of 15-20° C. for 48-72 hours;

4) transferring into 1/2MS medium, to continue to cultivate at 23° C.±2° C. with a lighting of 1000 Lux, 16 hours/day;

5) transplanting the seedlings in bottles into disinfected soil when the seedlings have developed into 4 true leaf stage and their roots have a length of 3-5 cm; at 3 days before transplanting, opening the caps of bottles for acclimatization; the transplanted seedlings must be carefully managed;

6) subjecting the newborn young leaves of F1 seed embryo to chromosome analysis and ploidy identification, removing chimeras and aneuploids, screening for homozygous tetraploid plants; and 7) subjecting the *Ricinus communis* L. tetraploids to large-scale planting and cultivation management according to conventional methods for cultivating *Ricinus communis* L., subjecting the F1 seeds of tetraploid *Ricinus communis* L. to chromosome analysis and ploidy identification again, removing chimeras and aneuploids, screening for a new homozygous tetraploid *Ricinus communis* L. germplasm.

5. The breeding method for tetraploid *Ricinus communis* L. according to claim 4, wherein the conventional disinfection method is as follows: disinfecting with 75% alcohol for 60 seconds, rinsing with sterile water, and then disinfecting with 2% sodium hypochlorite for 15 minutes, rinsing with sterile water for 3 times.

6. The breeding method for tetraploid *Ricinus communis* L. according to claim 4, wherein the mass percent concentrations of the colchicine and oryzalin solutions are 0.02%, respectively; and the final concentration of each of the mixed mutagens is 0.01%.

7. The breeding method for tetraploid *Ricinus communis* L. according to claim 4, wherein the conditions for the management of transplanted seedlings are as follows: maintaining the temperature at 25° C.±2° C., the humidity at 65%±5; the soil condition is normal sandy loams.

8. The breeding method for tetraploid *Ricinus communis* L. according to claim 4, wherein the steps of chromosome analysis and ploidy identification are as follows: harvesting newborn young leaves at 8-9 a.m., pre-processing with 0.002M 8-hydroxyquinoline for 3-4 hours, then preparing chromosome specimens of *Ricinus communis* L. through a wall degradation hypotonic method utilized in the preparation of chromosome specimens of plants, removing chimeric and aneuploid plants, screening for plants whose somatic cell chromosome is 2n=4x=40 to obtain homozygous tetraploid plants.

* * * * *